(12) United States Patent
Dutta Ray et al.

(10) Patent No.: US 12,042,642 B2
(45) Date of Patent: Jul. 23, 2024

(54) MUSCLE WIRE ESCAPEMENT ACTIVATION ASSEMBLY FOR A DRUG DELIVERY DEVICE

(71) Applicant: AMGEN INC., Thousand Oaks, CA (US)

(72) Inventors: Sudeshna Dutta Ray, Thousand Oaks, CA (US); Scott Robert Gibson, Granada Hills, CA (US); Daniel Eduardo Groszmann, Belmont, MA (US); Mehran Mojarrad, Thousand Oaks, CA (US); Andrew James Carlson, Thousand Oaks, CA (US); Lee Gordon Macklem, Thousand Oaks, CA (US); Mikhail Tikh, St. Louis Park, MN (US)

(73) Assignee: AMGEN INC., Thousand Oaks, CA (US)

( * ) Notice: Subject to any disclaimer, the term of this patent is extended or adjusted under 35 U.S.C. 154(b) by 721 days.

(21) Appl. No.: 17/264,157

(22) PCT Filed: Sep. 17, 2019

(86) PCT No.: PCT/US2019/051396
§ 371 (c)(1),
(2) Date: Jan. 28, 2021

(87) PCT Pub. No.: WO2020/068476
PCT Pub. Date: Apr. 2, 2020

(65) Prior Publication Data
US 2021/0228811 A1 Jul. 29, 2021

Related U.S. Application Data

(60) Provisional application No. 62/738,561, filed on Sep. 28, 2018.

(51) Int. Cl.
*A61M 5/315* (2006.01)
*A61M 5/142* (2006.01)
(Continued)

(52) U.S. Cl.
CPC .... *A61M 5/31576* (2013.01); *A61M 5/14248* (2013.01); *A61M 5/1452* (2013.01);
(Continued)

(58) Field of Classification Search
CPC ........... A61M 5/1452; A61M 5/14248; A61M 5/168; A61M 5/31576; A61M 2005/1585; A61M 2005/31588
See application file for complete search history.

(56) References Cited

U.S. PATENT DOCUMENTS

2010/0292651 A1* 11/2010 Yodfat ................ A61M 5/1454
604/218
2016/0038691 A1 2/2016 Mounce et al.

FOREIGN PATENT DOCUMENTS

EP 3260146 A1 12/2017
WO WO-2013078200 A1 5/2013
(Continued)

OTHER PUBLICATIONS

International Search Report and Written Opinion for International Application No. PCT/US2019/051396, dated Nov. 21, 2019.

*Primary Examiner* — Emily L Schmidt
*Assistant Examiner* — Samuel J Marrison
(74) *Attorney, Agent, or Firm* — MARSHALL, GERSTEIN & BORUN LLP; Michael P. Furmanek

(57) ABSTRACT

Drug delivery devices are described that include an escapement activation assembly. The escapement activation assembly includes a slide having a plurality of pallet engagement portions and a switch engagement portion and a pallet having a plurality of slide engagement portions. A drive is
(Continued)

coupled to the pallet to cause the pallet to move relative to the slide to move the plurality of slide engagement portions into and out of engagement with the plurality of pallet engagement portions to allow the slide to move along a path within the drug delivery device. Movement of the slide can cause the switch engagement portion to move out of engagement with an activation trigger of a mechanism of the drug delivery device.

18 Claims, 7 Drawing Sheets

(51) Int. Cl.
*A61M 5/145* (2006.01)
*A61M 5/158* (2006.01)

(52) U.S. Cl.
CPC ............... *A61M 2005/1585* (2013.01); *A61M 2005/31588* (2013.01); *A61M 2205/52* (2013.01)

(56) References Cited

FOREIGN PATENT DOCUMENTS

| WO | WO-2017118539 A1 | * | 7/2017 | .......... A61M 5/1452 |
| WO | WO-2018166703 A1 | * | 9/2018 | .............. A61M 5/20 |

\* cited by examiner

MUSCLE WIRE ESCAPEMENT ACTIVATION ASSEMBLY FOR A DRUG DELIVERY DEVICE

CROSS-REFERENCE TO RELATED APPLICATION

This is the United States national phase of International Patent Application No. PCT/US19/51396, filed Sep. 17, 2019, which claims priority to U.S. Provisional Patent Application No. 62/738,561, filed Sep. 28, 2018, the entire contents of each of which are hereby incorporated by reference.

FIELD OF THE DISCLOSURE

The present disclosure generally relates to drug delivery devices and, more particularly, to activation mechanisms for drug delivery devices.

BACKGROUND

Drugs can be administered through the use of drug delivery devices such as autoinjectors or on-body injectors. Autoinjectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological impediments.

Conventional on-body injectors can utilize a variety of drive mechanisms to operate components within the device, including needle insertion and plunger drives. One option is a DC servomotor having a worm drive first stage and spur gear driven cams and tabs. Another option is a stepper motor drive with a worm drive first stage and spur gear driven cams and tabs. With these options, the motors and components can require a relatively large footprint and volume for the gears and cams. Further, the motor and components can have many bearing surfaces, can require a large amount of power to operate and can require servo control. A third option is magnetic solenoids. This option, however, also can require a relatively large footprint and volume, as well as a large amount of power to operate.

SUMMARY

In accordance with a first aspect, a drug delivery device is described that includes an activation assembly. The activation assembly includes a slide, a pallet, and a drive coupled to the pallet. The slide includes a main wall portion with an elongate configuration, a plurality of pallet engagement points spaced from one another along a length of the slide, and a switch engagement portion. The slide is biased to move along a path within the drug delivery device. The pallet includes a plurality of slide engagement portions and is mounted within the drug delivery device so that at least one of the plurality of slide engagement portions engage at least one of the plurality of pallet engagement portions of the slide. Operation of the drive causes the pallet to move relative to the slide to move the plurality of slide engagement portions into and out of engagement with the plurality of pallet engagement portions to thereby allow the slide to move along the path from a first position to a second position and movement of the slide causes the switch engagement portion to move out of engagement with an activation trigger of a mechanism of the drug delivery device.

According to some forms, a first operation of the drive causes the pallet to move relative to the slide in a first direction to move individual ones of the plurality of slide engagement portions into and out of engagement with individual ones of the plurality of pallet engagement portions to thereby allow the slide to move along the path from a first position to a second position and a second operation of the drive causes the pallet to move relative to the slide in a second, opposite direction to move individual ones of the plurality of slide engagement portions into and out of engagement with individual ones of the plurality of pallet engagement portions allowing the slide to move along the path from the second position to a third position.

According to some forms, the switch engagement portion can be a first switch engagement portion, the slide can further include a second switch engagement portion, and movement of the slide can cause the first switch engagement portion to move out of engagement with an activation trigger of a first mechanism of the drug delivery device and the second switch engagement portion to move out of engagement with an activation trigger of a second mechanism of the drug delivery device. In further forms, operation of the drive can cause the pallet to move relative to the slide to move the plurality of slide engagement portions into and out of engagement with the plurality of pallet engagement portions to thereby sequentially allow the slide to move along the path from the first position to the second position to a third position to a fourth position and movement of the slide from the first position to the second position can cause the first switch engagement portion to move out of engagement with the activation trigger of the first mechanism and movement of the slide from the third position to the fourth position can cause the second switch engagement portion to move out of engagement with the activation trigger of the second mechanism. In some forms, the drug delivery device can include a cannula insertion device including a cannula and a drive assembly coupled to the cannula that is configured to shift the cannula downward during an injection operation, where the drive assembly has a release engaged by the first switch engagement portion of the slide in the first position and released by the first switch engagement portion in the second position. In some forms, the drug delivery device can include a plunger rod drive having a release engaged by the second switch engagement portion of the slide in the first, second, and third positions and released by the second switch engagement portion in the fourth position. In yet further forms, the slide can include a shelf extending outwardly from the main wall portion, where the shelf includes the first switch engagement portion and, optionally, the main wall portion includes the second switch engagement portion. If desired, the slide can further include a tab portion that extends from the shelf, where the tab portion is configured to engage the cannula with the slide in the first position and release the cannula with the slide in the second position.

According to some forms, the drive can include a muscle wire having an anchored first end and a second end coupled to the pallet and the pallet can be rotatably mounted within the drug delivery device, such that the first operation includes a first contraction of the muscle wire in response to reception of an electrical current that causes the pallet to rotate in a first direction to move a first one of the plurality of slide engagement portions out of engagement with a first one of the pallet engagement portions allowing the slide to move along the path from the first position until a second one of the plurality of pallet engagement portions engages a second one of the plurality of slide engagement portions to the second position. In a further form, the drive can include a biasing mechanism coupled to the pallet to bias the pallet to rotate in a second, opposite direction such that disconnection of the electrical current from the muscle wire causes the pallet to move in the second direction to move the second one of the plurality of slide engagement portions out of engagement with the second one of the pallet engagement portions allowing the slide to move along the path from the second position until a third one of the plurality of pallet engagement portions engages the first one of the plurality of slide engagement portions to a third position. In yet a further form, a second contraction of the muscle wire causes the pallet to rotate in the first direction to move the first one of the plurality of tabs out of engagement with the third one of the pallet stops allowing the slide to move along the path from the third position to a fourth position.

In accordance with a second aspect, a method for operating a drug delivery device is described that includes engaging an activation trigger of a mechanism of the drug delivery device with a switch engagement portion of a slide, and operating a drive to cause a pallet to move relative to the slide to move a plurality of slide engagement portions of the pallet into and out of engagement with a plurality of pallet engagement portions of the slide to thereby shift the slide along a path. Shifting the slide along the path moves the switch engagement portion of the slide out of engagement with the activation trigger of the mechanism of the drug delivery device to thereby activate the mechanism.

According to some forms, operating the drive to cause the pallet to move relative to the slide to move the plurality of slide engagement portions of the pallet into and out of engagement with the plurality of pallet engagement portions of the slide to thereby shift the slide along the path can include operating the drive to cause the pallet to move relative to the slide in a first direction to move individual ones of the plurality of slide engagement portions into and out of engagement with individual ones of the plurality of pallet engagement portions to thereby allow the slide to move along the path from a first position to a second position; and operating the drive to cause the pallet to move relative to the slide in a second, opposite direction to move individual ones of the plurality of slide engagement portions into and out of engagement with individual ones of the plurality of pallet engagement portions allowing the slide to move along the path from the second position to a third position.

According to some forms, the switch stop can be a first switch stop, the mechanism of the drug delivery device can be a first mechanism of the drug delivery, and the slide can include a second switch stop, such that shifting the slide along the path moves the first switch engagement portion of the slide out of engagement with the activation trigger of the first mechanism of the drug delivery device to activate the first mechanism and subsequently moves the second switch engagement portion of the slide out of engagement with an activation trigger of a second mechanism of the drug delivery device to activate the second mechanism. In a further form, activing the first mechanism can include activating a cannula insertion device including a cannula and a drive assembly configured to shift the cannula downward during an injection operation; and activating the second mechanism can include activating a plunger rod drive. In yet a further form, the method can include engaging the cannula with a tab portion of the slide; and wherein moving the first switch engagement portion of the slide out of engagement with the activation trigger of the cannula insertion device further comprises moving the tab portion of the slide out of engagement with the cannula.

According to some forms, the drive can be a muscle wire having an anchored first end and a second end coupled to the pallet and the pallet can be rotatably mounted within the drug delivery device. In these forms, operating the drive to cause the pallet to move relative to the slide to move the plurality of slide engagement portions of the pallet into and out of engagement with the plurality of pallet engagement portions of the slide to thereby shift the slide along the path can include directing an electrical current to the muscle wire to cause the pallet to rotate in a first direction to move a first one of the plurality of slide engagement portions out of engagement with a first one of the pallet engagement portions allowing the slide to move along the path from the first position until a second one of the plurality of pallet engagement portions engages a second one of the plurality of slide engagement portions to the second position. In a further form, the method can include disconnecting the electrical current from the muscle wire, such that a biasing member causes the pallet to move in an opposite, second direction to move the second one of the plurality of slide engagement portions of the pallet out of engagement with the second one of the pallet engagement portions of the slide; and shifting the slide along the path from the second position until a third one of the plurality of pallet engagement portions engages the first one of the plurality of slide engagement portions to a third position. In yet a further form, the method can include directing an electrical current to the muscle wire to cause a second contraction of the muscle wire to cause the pallet to rotate in the first direction to move the first one of a plurality of slide engagement portions of the pallet out of engagement with the third one of the plurality of pallet engagement portions of the slide; and shifting the slide along the path from the third position to a fourth position.

In accordance with a third aspect, a drug delivery device is described herein that includes an escapement activation assembly. The activation assembly includes a slide having a main wall portion with an elongate configuration, a plurality of pallet stops spaced from one another along a length of the slide, and a switch stop. The slide is biased to move along an axis within the drug delivery device. The activation assembly further includes a pallet having a plurality of outwardly projecting tabs and muscle wire having an anchored first end and a second end coupled to the pallet. The pallet is rotatably mounted within the drug delivery device so that the plurality of tabs can selectively extend into a travel path of the plurality of pallet stops. A first contraction of the muscle wire in response to reception of an electrical current causes the pallet to rotate in a first direction to move a first one of the plurality of tabs out of engagement with a first one of the pallet stops allowing the slide to move along the axis from a first position until a second one of the plurality of pallet stops engages a second one of the plurality of tabs to a second position. Further, movement of the slide causes the switch stop to move out of engagement with an activation trigger of a mechanism of the drug delivery device.

According to some forms, the main wall portion of the slide can be planar, can extend along the axis, and can include the plurality of pallet stops. Further, the main wall portion can include the switch stop.

In some versions, the slide can include a shelf that extends outwardly from the main wall portion and includes the switch stop. In further forms, the drug delivery device can include a cannula insertion device having a cannula and a drive assembly that is coupled to the cannula and that is configured to shift the cannula downward during an injection operation. In these forms, the drive assembly can have a release that is engaged by the switch stop of the shelf with the slide in the first position and released by the switch stop of the shelf with the slide in the second position. If desired, the slide can further include a tab portion that extends upwardly from the shelf and that is configured to engage the cannula with the slide in the first and release the cannula with the slide in the second position.

According to some forms, the pallet can be biased to rotate in a second, opposite direction such that disconnection of the electrical current from the muscle wire causes the pallet to move in the second direction to move the second one of the plurality of tabs out of engagement with the second one of the pallet stops allowing the slide to move along the axis from the second position until a third one of the plurality of pallet stops engages the first one of the plurality of tabs to a third position. In these forms, a second contraction of the muscle wire can cause the pallet to rotate in the first direction to move the first one of the plurality of tabs out of engagement with the third one of the pallet stops allowing the slide to move along the axis from the third position to a fourth position. Further, in some instances, the switch stop can be a first switch stop and the assembly can include a second switch stop. In these instances, the drug delivery deliver device can include a plunger rod drive having a release engaged by the second switch stop of the slide in the first, second, and third positions and released by the second switch stop in the fourth position.

In accordance with a fourth aspect, a method for operating a drug delivery device is described herein that includes engaging an activation trigger of a mechanism of the drug delivery device with a switch stop of a slide, directing an electrical current to a muscle wire to cause a first contraction of the muscle wire to cause a pallet to rotate in a first direction to move a first one of a plurality of tabs of the pallet out of engagement with a first one of a plurality of pallet stops of the slide, shifting the slide along a linear path from a first position until a second one of the plurality of pallet stops engages a second one of the plurality of tabs of the slide to a second position, and moving the switch stop of the slide out of engagement with the activation trigger of the mechanism of the drug delivery device to activate the mechanism.

According to some forms, shifting the slide along the linear path can include moving the slide along the linear path with a biasing mechanism, the method can include biasing the pallet to rotate in a second direction opposite of the first direction with a second biasing member, and/or engaging the activation trigger of the mechanism of the drug delivery device can include engaging the activation trigger with the switch stop of a shelf extending outwardly from a main wall portion of slide.

In some versions, moving the switch stop of the slide out of engagement with the activation trigger of the mechanism can include moving the switch stop of the slide out of engagement with an activation trigger of a cannula insertion device and the method can further include operating the cannula insertion device to drive a cannula downward during an injection operation. In further versions, the method can include engaging the cannula with a tab portion of the slide extending upwardly from the shelf and moving the switch stop of the slide out of engagement with the activation trigger of the mechanism of the drug delivery device can include moving the tab portion of the slide out of engagement with the cannula.

According to some forms, the method can include disconnecting the electrical current from the muscle wire, such that the second biasing member causes the pallet to move in the second direction to move the second one of the plurality of tabs out of engagement with the second one of the pallet stops and shifting the slide along the linear path from the second position until a third one of the plurality of pallet stops engages the first one of the plurality of tabs to a third position. In further forms, the method can include directing an electrical current to the muscle wire to cause a second contraction of the muscle wire to cause the pallet to rotate in the first direction to move the first one of a plurality of tabs of the pallet out of engagement with the third one of the plurality of pallet stops of the slide and shifting the slide along the linear path from the third position to a fourth position. In yet further forms, the slide can further include a second switch stop and the method can further include engaging a release of a plunger rod drive of the drug delivery device with the second switch stop in the first, second, and third positions and moving the second switch stop of the slide out of engagement with the release of the plunger rod drive with movement of the slide to the fourth position.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

Activation assemblies, drug delivery devices, methods, and components are described that utilize an escapement assembly to activate one or more components for an injection operation. The escapement assembly includes a slide and a pallet configured to move with respect to one another to sequentially advance the slide within the drug delivery device. The slide can engage a release of the one or more components in one position and disengage from the release in another position allowing the component to activate, including allowing a drive within the component to drive insertion of a cannula or drive a plunger rod through a drug reservoir. The escapement assembly described herein can trigger multiple discrete functions for the drug delivery device during an injection operation with a single active element using inexpensive materials and parts.

Movement of the escapement assembly can be achieved through muscle wire and biasing elements, such as tension springs. One biasing element can bias the slide to move along a linear path. Another biasing element can bias the pallet to rotate in one direction and the muscle wire can be configured to rotate the pallet in an opposite direction. So configured, activation of the drug delivery device components can be achieved by selectively sending a current through the muscle wire to cause the pallet to rotate back and forth, into and out of engagement with the slide, allowing the slide to move along the linear path. Selectively pulsing a muscle wire to trigger the escapement assembly offers several advantages over the above conventional forms. For example, the escapement assembly utilizes less space, has fewer bearing surfaces, requires less power and servo control, and does not utilize gearing for multiplication or reduction of motion. Further, devices utilizing the escapement assembly can allow simultaneous action on multiple planes with tabs and cams, can be reset or reloaded, can operate quietly, can have zero power uses before and between actions, can operate without closed loop control other than a failsafe detection, and can be easily scaled for any size or required load.

Figure 1:
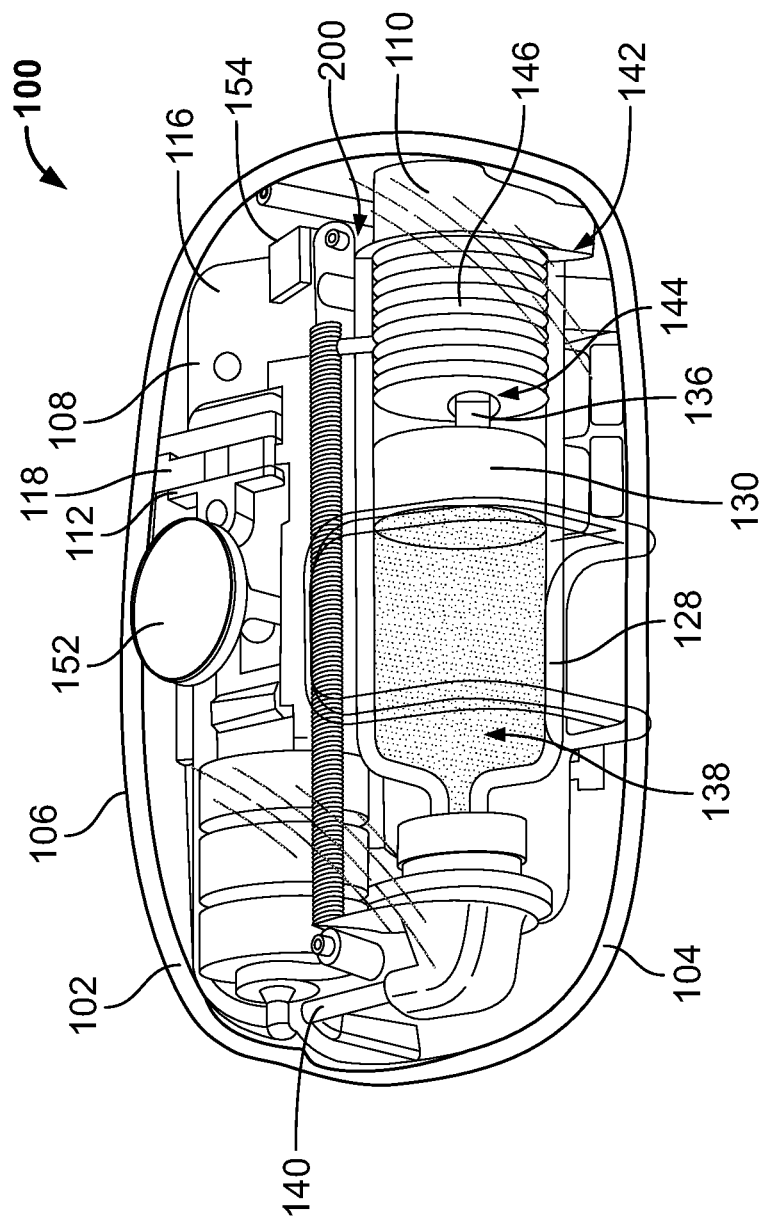
FIG. 1 is a perspective view of a drug delivery device having an escapement assembly in accordance with various embodiments.

An example on-body injector drug delivery device 100 is shown in FIG. 1. The drug delivery device 100 includes a housing 102 having a generally planar bottom wall 104 and a upper housing portion 106, which can have an ergonomically domed configuration as shown. The components of the drug delivery device 100 include a needle and cannula insertion mechanism (NIM) 108 and a plunger drive mechanism 110.

Figure 9:
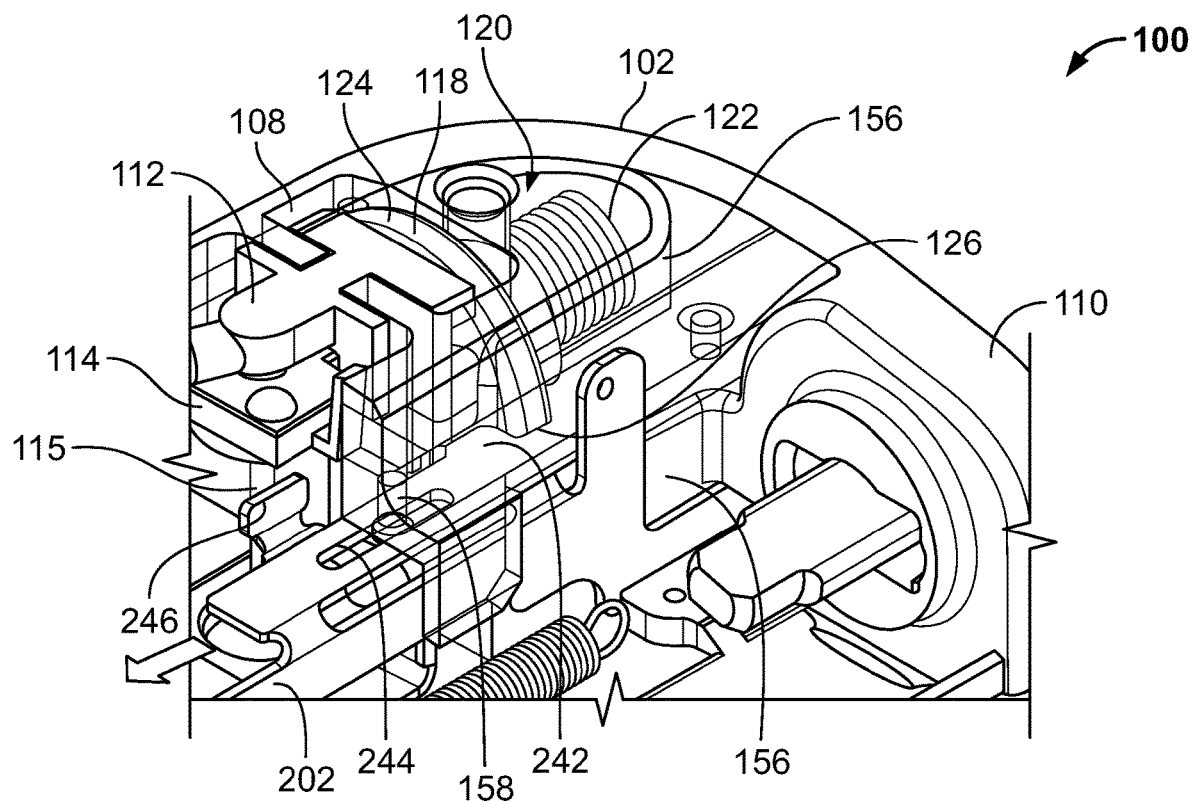
FIG. 9 is a sectional perspective view of a drug delivery device with the escapement assembly of FIG. 8 disposed therein to activate a needle insertion mechanism in accordance with various embodiments.

As shown in FIGS. 1 and 9, the NIM 108 can be a scotch yoke mechanism that includes a needle sliding member 112 having a needle or trocar mounted thereto and a cannula sliding member 114 having a cannula 115 mounted thereto. The members 112, 114 are coupled to and project forwardly from a housing 116 of the NIM 108. The members 112, 114 are operably coupled to a crank 118 and a drive 120 of the NIM 108, as commonly configured, so that rotation of the crank 118 drives linear movement of the members 112, 114 downwardly toward a patient. In the illustrated form, the drive 120 includes a torsion spring 122. In other embodiments, the drive 120 can include pneumatics, hydraulics, a motor, and/or a mechanical linkage. The drive 120 further includes a release member 124 that is operably coupled to the torsion spring 122, such that engagement of the release member 124 prevents release of the torsion spring 122. In some versions, the release member 124 is coupled to the torsion spring 122 to rotate therewith and includes an outwardly extending stop surface 126. For example, the stop surface 126 can extend in a radial direction. In other versions, the release member 124 can be a switch device operably coupled to a release linkage. So configured, the drive 120 can be held in a charged state by engaging the stop surface 126 and preventing rotation of the release member 124 and release of the torsion spring 122.

In use, the NIM 108 is configured to insert the trocar 113 and cannula 115 through an opening in the bottom wall 104 and into subcutaneous tissue of a patient when activated. The members 112, 114 can have separate couplings to the NIM 108 or the NIM 108 can drive the needle member 112 with the needle member 112 driving movement of the cannula member 114. The NIM 102 inserts the trocar 113 to a designed depth in subcutaneous tissue and then retracts the trocar 113 with the cannula 115 held in an inserted state during operation of the device 100.

Figure 13:
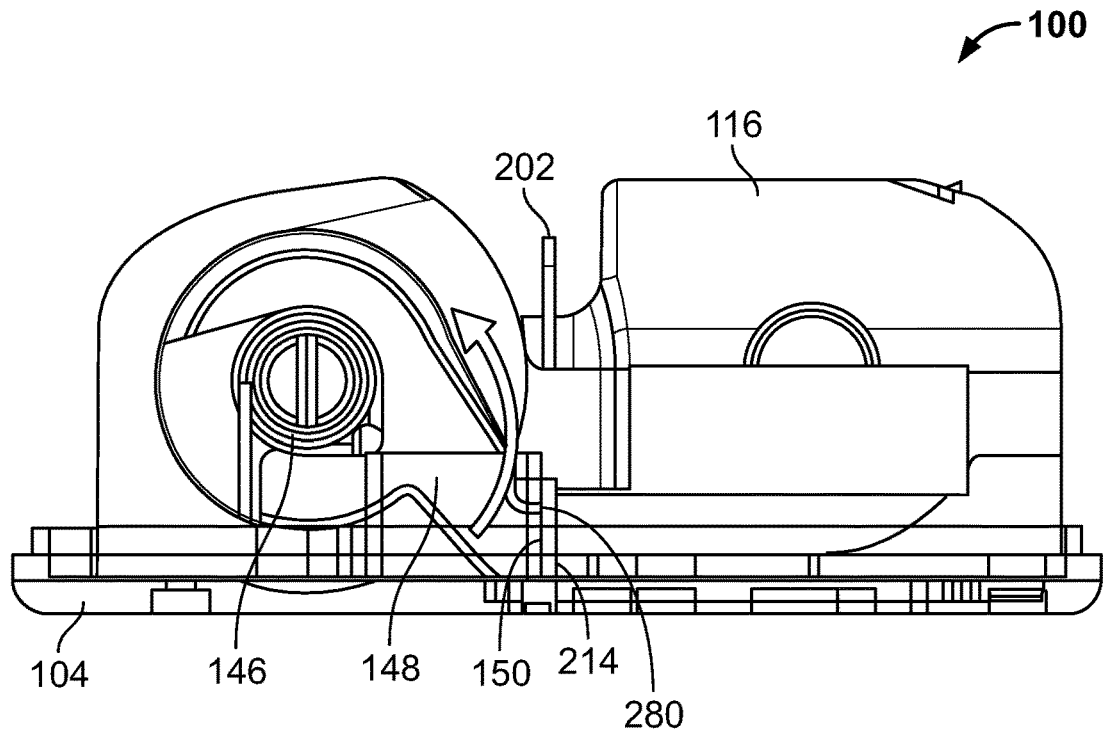
FIG. 13 is a side plan view of the drug delivery device of FIG. 12 in accordance with various embodiments

As shown in FIGS. 1 and 13, the drug delivery device 100 further includes a reservoir 128 having a tubular configuration, a stopper 130 disposed within an interior 132 of the reservoir 134, and a plunger rod 136 configured to engage and push the stopper 130 through the reservoir 128 to thereby expel a drug 138 from the reservoir interior 132. The drug 138 is expelled from the reservoir 128 into a flow path 140 fluidly coupling the reservoir 128 and the trocar 113 and cannula 115. The flow path 140 can include any suitable conduits, couplings, valves, sensors, and connectors as desired.

The plunger drive mechanism 110 includes a drive 142 and a plunger rod coupling 144. In the illustrated form, the drive 142 includes a torsion spring 146. In other embodiments, the drive 142 can include pneumatics, hydraulics, a motor, and/or a mechanical linkage. The drive 142 further includes a release member 148 that is operably coupled to the torsion spring 146, such that engagement of the release member 148 prevents release of the torsion spring 146. In some versions, the release member 148 is coupled to the torsion spring 146 to rotate therewith and includes an outwardly extending stop surface 150. For example, the stop surface 150 can be provided by a foot extension 152 of the release member 140 to extend in a direction generally parallel with a tangent of the torsion spring 146. In other versions, the release member 148 can be a switch device operably coupled to a release linkage.

So configured, after the NIM 108 inserts the needle 113 and cannula 115 and retracts the needle 113, the device 100 can then operate the plunger drive mechanism 110. The drive 142 can be held in a charged state by engaging the stop surface 150 and preventing rotation of the release member 148 and release of the torsion spring 146. Upon activation, the torsion spring 146 of the plunger drive mechanism 110 moves the plunger rod 136 via the plunger rod coupling 144 longitudinally through the reservoir 128 until the plunger rod 136 engages and pushes the stopper 130 through the reservoir 128 to dispense the drug 138. The coupling 130 can engage the plunger rod 136 by threading or other suitable connections.

The components of the device 100 may be operated in response to user actuation of a user input 152 shown in FIG. 1, which can take any suitable form, including a push button switch, slide switch, touch screen, and so forth, by a controller 154. In further approaches, the controller 154 can have a timed delay to operate the components of the device 100 in response to user actuation of the user input 152. The controller 154 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 154 may include other circuitry for carrying out certain actions in accordance with the principles of the present disclosure.

Activation of the NIM 108 and the plunger drive mechanism 110 can be controlled by an escapement assembly 200, details of which are shown in FIGS. 2-13. The escapement assembly 200 includes a slide member 202 and a pallet 204 that selectively engages the slide 202 while the slide 202 is biased to shift along a linear path to allow the slide 202 to sequentially advance through the housing 102 along the linear path.

Figure 2:
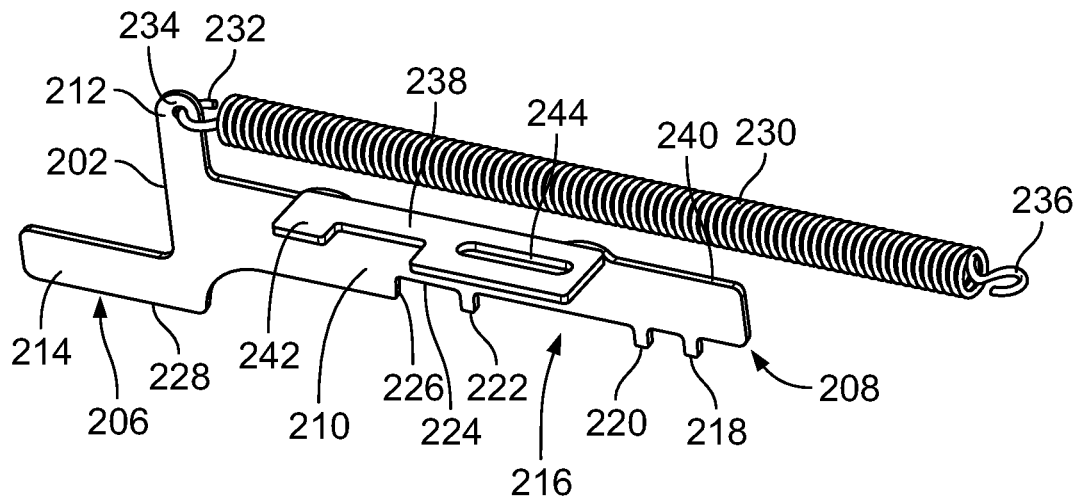
FIG. 2 is a perspective view of a slide and biasing spring for an escapement assembly in accordance with various embodiments.

Details of the slide 202 are shown in FIG. 2. The slide 202 extends between proximal and distal ends 206, 208 and includes a main wall portion 210 including a biasing mount 212 and a foot 214 at the proximal end 208. The slide main wall 210 includes a pallet engagement recess 216 adjacent to the distal end 206 with pallet engagement portions 218, 220, 222, 226. In the illustrated form, the pallet engagement portions 218, 220, 222, 226 are stops having surfaces that project downwardly from a bottom edge 224 of the main wall 210. The pallet stops 218, 220, 222, 226 are disposed and configured to sequentially engage the pallet 204 during operation of the drug delivery device 100, as described in more detail below. The palette stops 218, 220, 222, 226 are spaced from one another along a length of the bottom edge 224. In the illustrated form, the first and second palette stops 218, 220 are grouped closely together with the third and fourth pallet stops 222, 226 grouped closely together and spaced from the first and second pallet stops 218, 220 due to the configuration of the pallet 204. Although the stops shown include a tab structure, other structures suitable for engaging the pallet 204 can alternatively be utilized.

As shown, the foot 214 extends from the main wall 210 to the proximal end 208 of the slide 202. In the illustrated form, the foot 214 is vertically offset from the main wall 210 such that a bottom edge 228 is disposed below the pallet stops 218, 220, 222. With this configuration, the foot bottom edge 228 can slide along the housing bottom wall 104 and the pallet stops 218, 220, 222 are spaced therefrom, allowing the pallet 204 to be positioned between the engagement recess 216 and the bottom wall 104. Further, the foot 214 and main wall 210 can be integral with one another and/or co-planar.

As briefly discussed above, the slide 202 is biased within the device housing 102 to shift along a linear path. Pursuant to this, the escapement assembly further includes a first biasing member 230 coupled to the biasing mount 212 to bias the slide 202 along the linear path. In the illustrated form, the first biasing member 230 is a tension spring having one end 232 secured to an opening 234 in the biasing mount 212. The other end 236 of the first biasing member 230 can be secured to the housing 102 or other structure within the device 100 so that the first biasing member 230 extends along the linear path and is held in an expanded state to pull the slide 202 along the linear path. The biasing mount 212 can project upwardly from the main wall 210 and foot 214 to provide clearance for the spring 230 to extend over the other portions of the slide 202. Of course, other configurations, and biasing mechanisms, such as compression springs, pressurized gas, and so forth, are within the scope of this disclosure.

As shown in FIG. 2, the slide 202 can further include a shelf portion 238 that extends outwardly from an intermediate portion of a top edge 240 of the main wall 210 to extend an engagement width of the slide 202. As shown, the shelf 238 can include a switch engagement portion 242 and an elongate slot opening 244 extending therethrough. In some versions, the slide 202 can also include a cannula engagement tab 246 (FIG. 9) that projects upwardly from the shelf 238. Although the illustrated form includes a switch engagement portion 242 on the shelf 238, it will be readily understood that the switch engagement portion 242 could alternatively be provided on the main wall 210.

Figure 3:
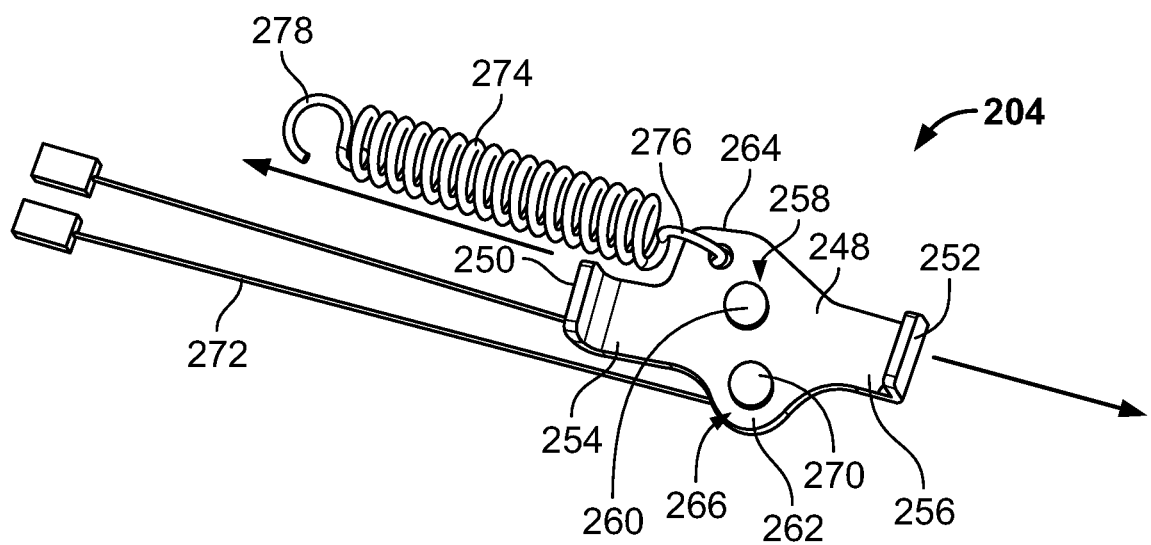
FIG. 3 is a perspective view of a pallet, biasing spring, and muscle wire for an escapement assembly in accordance with various embodiments.

An example configuration for the pallet 204 is shown in FIG. 3. The pallet 204 includes a main wall portion 248 with first and second slide engagement portions 250, 252. In the illustrated form, the slide engagement portions 250, 252 are tabs that project upwardly from the main wall 248 at proximal and distal ends 254, 256 thereof. The main wall 248 further includes a central, rotation connection 258. In the illustrated form, the connection 258 is a through opening sized to receive a pin connector 260 therethrough so that the pallet 204 is rotatable about the pin connector 260. The first and second tabs 250, 252 are offset from one another across the main wall 248 so that when one of the tabs 250, 252 is in the path of the pallet stops 218, 220, 222, the other of the tabs 250, 252 is disposed laterally outwardly of the linear path. With this configuration, rotation of the pallet 204 selectively moves one of the tabs 250, 252 into and out of the path of the pallet engagement portions 218, 220, 222, 226. In other forms, the pallet 204 can be configured to be shifted laterally within the housing 102.

The main wall 236 includes first and second wings 262, 264 projecting laterally outwardly from the central connection 258. The first wing 262 includes a muscle wire connection 266, which in the illustrated form, is a through opening sized to receive a pin connector 270 therethrough. The second wing 264 includes a biasing member connection 268. As briefly discussed above, the pallet 204 is configured to be selectively rotated. Pursuant to this, the pallet 204 is biased within the device housing 102 to rotate in a predetermined direction, while also being connected to a mechanism configured to rotate the pallet 204 in a direction opposite to the predetermined direction. In some versions, to provide this functionality, the escapement assembly 200 further includes a drive coupled to the pallet 204 and configured to move the pallet 204 relative to the slide 202. In the illustrated form, the drive includes a muscle wire 272 coupled to the pin connector 270 of the connection 266 of the first wing and a second biasing member 274 coupled to the connection 268 of the second wing 264. With this configuration, the second biasing member 274 biases the pallet 204 in a counterclockwise direction and the muscle wire 272, when contracted, rotates the pallet 204 in a clockwise direction over the biasing force of the second biasing member 274. In some examples, the second biasing member 274 can be a tension spring having one end 276 secured to the connection 268, which can be an opening as shown. The other end 278 of the second biasing member 274 can be secured to the housing 102 or other structure within the device 100 so that the second biasing member 274 is held in an expanded state to bias the pallet 204. Of course, other configurations, drives, such as motors and the like, and biasing mechanisms, such as compression springs, pressurized gas, and so forth, are within the scope of this disclosure.

Figure 4:
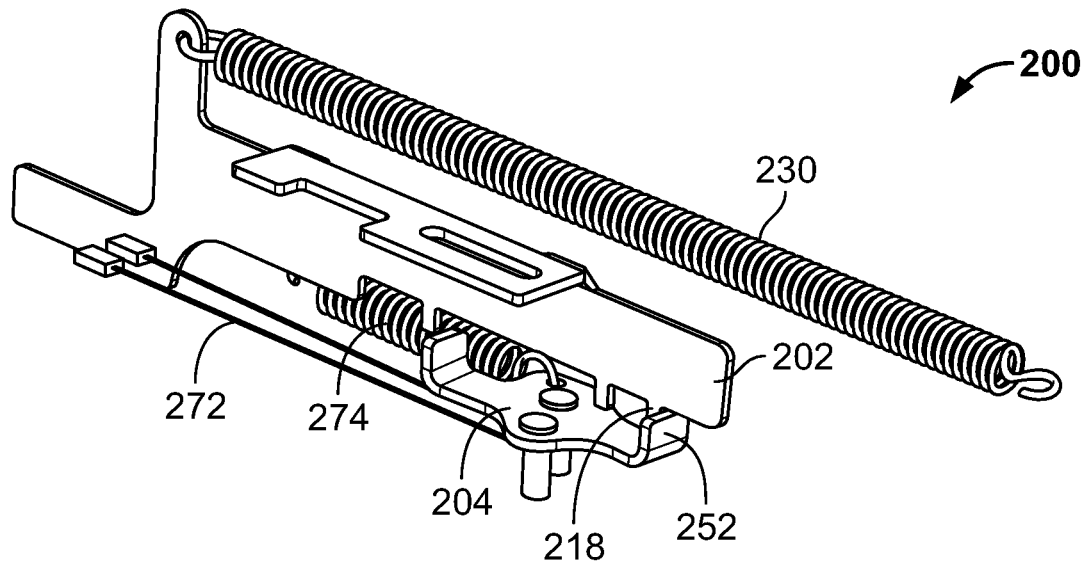
FIG. 4 is a perspective view of an escapement assembly with the slide of FIG. 2 in a first position and the pallet of FIG. 3 in a counterclockwise position in accordance with various embodiments.
Figure 5:
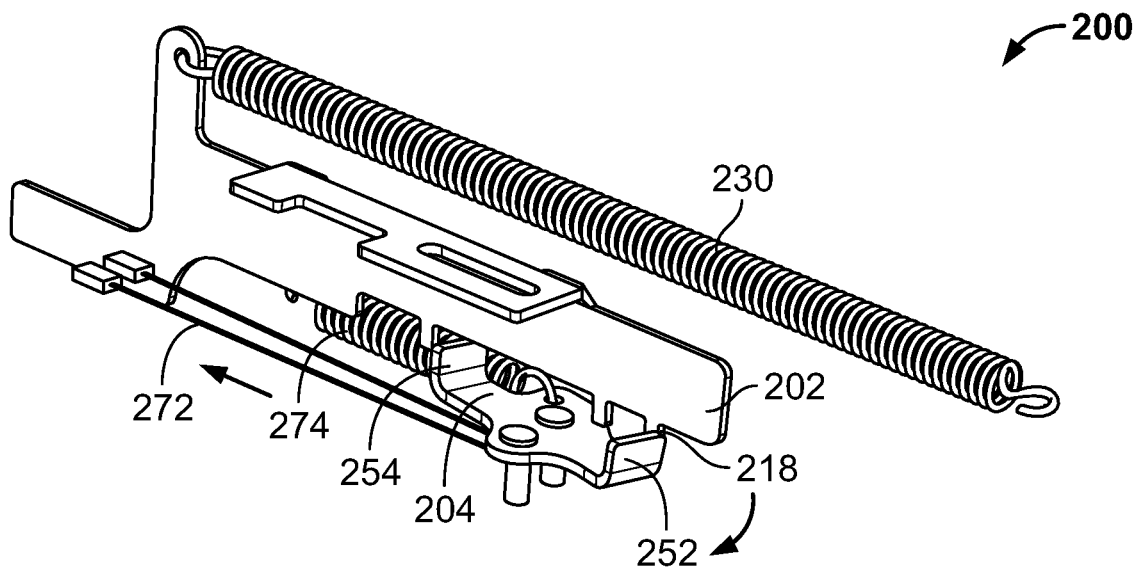
FIG. 5 is a perspective view of the escapement assembly of FIG. 4 with the slide of FIG. 2 in the first position and the pallet of FIG. 3 rotated to a clockwise position in accordance with various embodiments.
Figure 6:
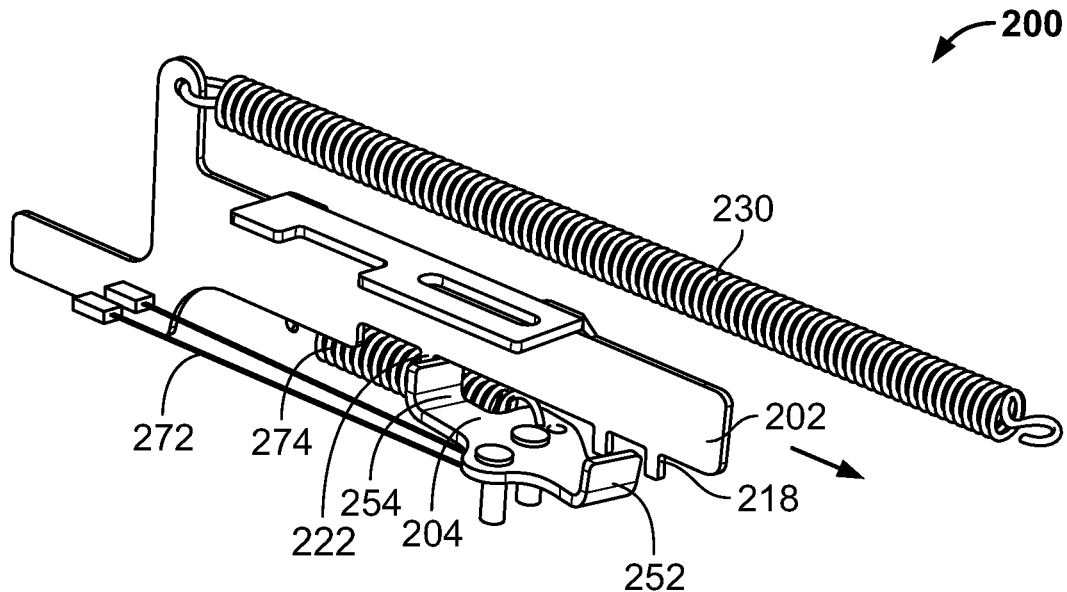
FIG. 6 is a perspective view of the escapement assembly of FIG. 4 with the slide of FIG. 2 shifted to a second position and the pallet of FIG. 3 in the clockwise position in accordance with various embodiments.
Figure 7:
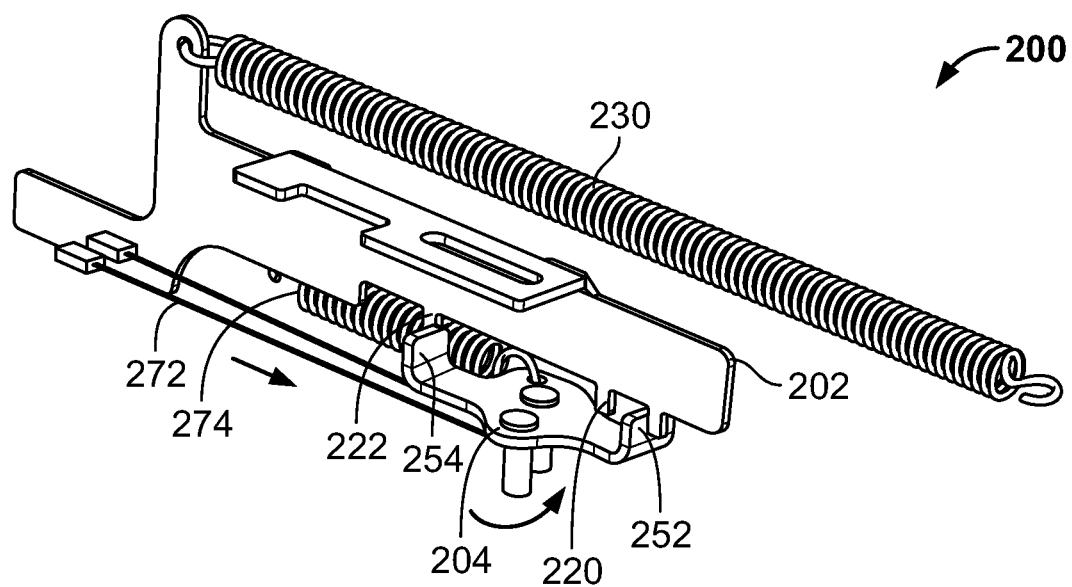
FIG. 7 is a perspective view of the escapement assembly of FIG. 4 with the slide of FIG. 2 in the second position and the pallet of FIG. 3 rotated to the counterclockwise position in accordance with various embodiments.
Figure 8:
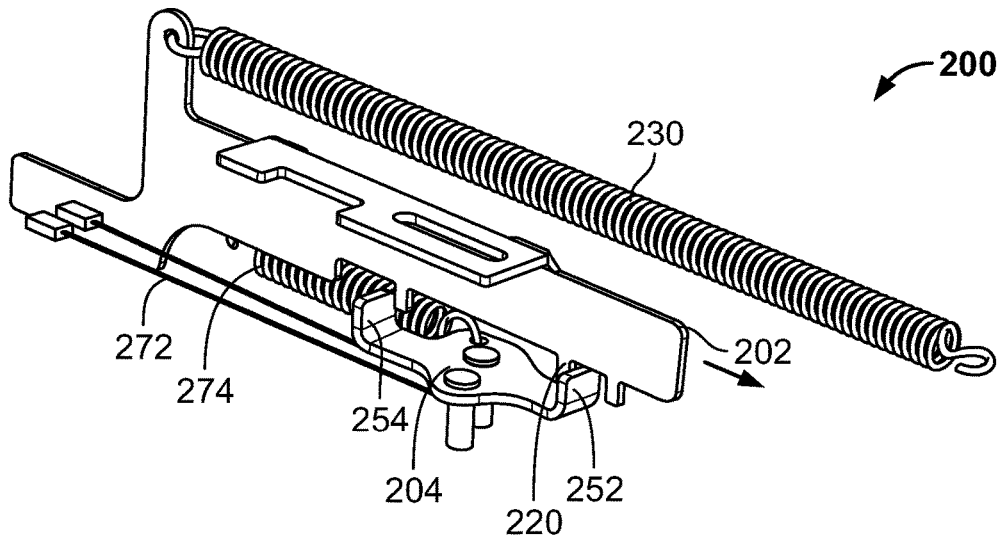
FIG. 8 is a perspective view of the escapement assembly of FIG. 4 with the slide of FIG. 2 shifted to a third position and the pallet of FIG. 3 in the counterclockwise position in accordance with various embodiments.

Operation of the escapement assembly 200, and through movement of the escapement assembly 200, of the drug delivery device 100 will now be described with reference to FIGS. 4-13. FIG. 4 illustrates the escapement assembly 200 in a first, unactivated position. In this first state, the muscle wire 272 is in an uncontracted state and the spring 274 holds the pallet 204 in a counterclockwise position with the distal tab 252 engaging the first pallet stop 218 and holding the slide 202 stationary. Upon activation of the device 100 by a user actuating the user input 152 or by timed release, the controller 154 directs a current to the muscle wire 272, which causes the muscle wire 272 to contract. Contraction of the muscle wire 272 causes the pallet 204 to rotate in a clockwise direction via the connection 266 until the distal tab 252 is moved out of the path of the first pallet stop 218 and the proximal tab 250 is moved into the path of the third pallet stop 222 as shown in FIG. 5. The spring 230 pulls the slide 202 along the linear path until the third pallet stop 222 abuts the proximal tab 250 corresponding to a second position as shown in FIG. 6. Thereafter, when the controller 154 disconnects the current from the muscle wire 272, the spring 274 rotates the pallet 204 in the counterclockwise direction, moving the proximal tab 250 out of engagement with the third pallet stop 222 and the distal tab 252 into the path of the second pallet stop 220 as shown in FIG. 7. The spring 230 then pulls the slide 202 along the linear path until the second pallet stop 220 abuts the distal tab 252 corresponding to a third position as shown in FIG. 8.

Turning now to FIG. 9, the escapement assembly 200 is shown in a portion of the drug delivery device 100. In the first and second positions, the switch engagement portion 242 of the shelf 238 is disposed underneath the stop surface 126 of the release member 124 of the NIM 108 preventing release of the torsion spring 122 and the cannula engagement tab 246, if utilized, is disposed beneath a portion of the cannula 115 preventing downward movement of the cannula 115. As shown, due to the radially extending stop surface 126, the shelf 238 can be disposed at a generally horizontal orientation and be disposed in a radial direction with respect to the release member 124 of the NIM 108. Accordingly, when the slide 202 is shifted to the third position, as shown in FIG. 9, the shelf 238 is also shifted, which moves the switch engagement portion 242 out of engagement with the stop surface 126 and the tab 246 out of engagement with the cannula 115. Thereafter, the torsion spring 122 releases and drives operation of the NIM 108 to insert the trocar 113 and the cannula 115, and remove the trocar 113.

As shown in FIG. 9, the slide 202 is disposed in an upright orientation with the main wall 210 and foot 214 extending generally perpendicular, e.g., within 1-5 degrees, to the bottom wall 104. The device 100 can further include one or more bracing members 156 to abut and position the slide 202 within the housing 102. If desired, to further ensure positioning, one of the bracing members 156 can include a pin 158 configured to project into the slot opening 244 of the shelf 238 and shift within the slot opening 244 as the slide 202 is shifted along the linear path.

Figure 10:
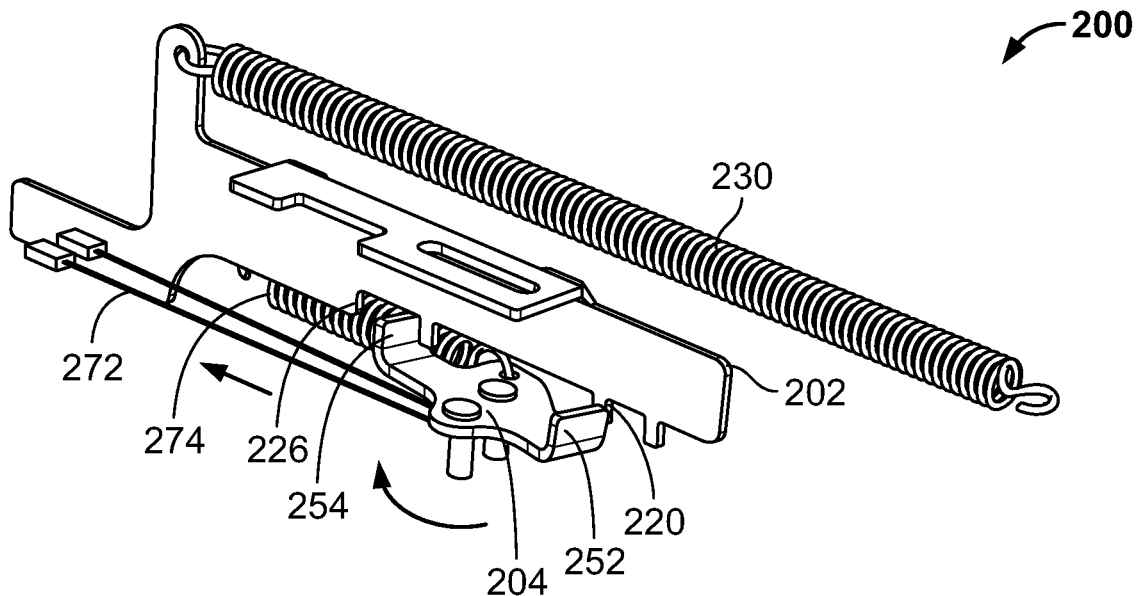
FIG. 10 is a perspective view of the escapement assembly of FIG. 4 with the slide of FIG. 2 in the third position and the pallet of FIG. 3 rotated to the clockwise position in accordance with various embodiments
Figure 11:
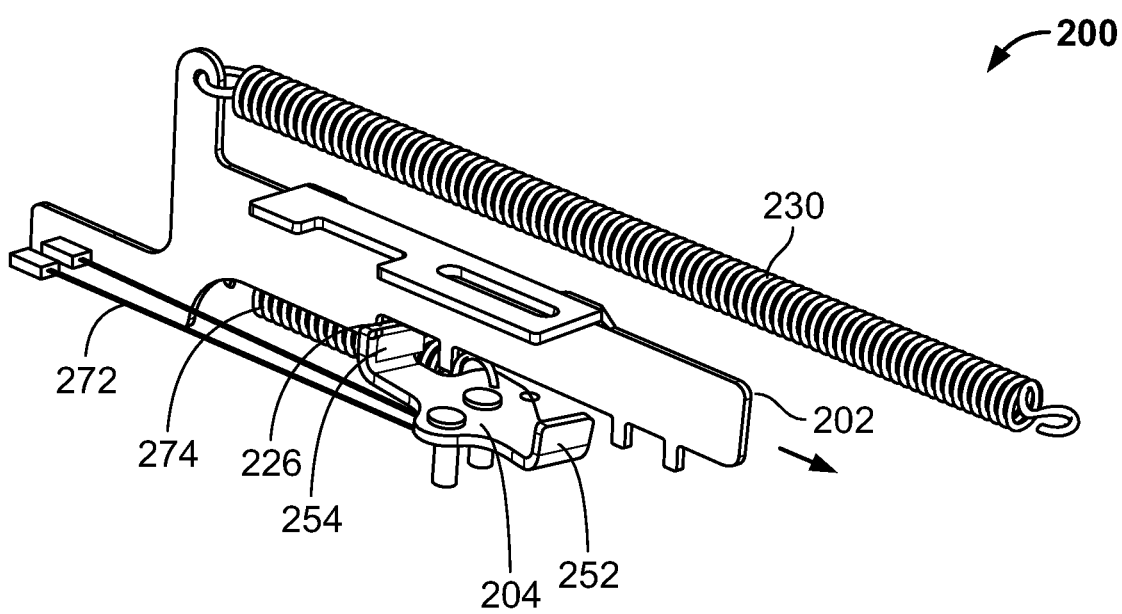
FIG. 11 is a perspective view of the escapement assembly of FIG. 4 with the slide of FIG. 2 shifted to a fourth position and the pallet of FIG. 3 in the clockwise position in accordance with various embodiments.

With the cannula 115 inserted into the patient, the controller 154 can again direct a current to the muscle wire 272, causing the muscle wire 272 to contract and rotate the pallet 204 in the clockwise direction until the distal tab 252 is moved out of engagement with the second pallet stop 220 and the proximal tab 250 is moved into the path of the fourth pallet stop 228 as shown in FIG. 10. The spring 230 pulls the slide 202 along the linear path until the fourth pallet stop 228 abuts the proximal tab 250 corresponding to a fourth position as shown in FIG. 11.

Figure 12:
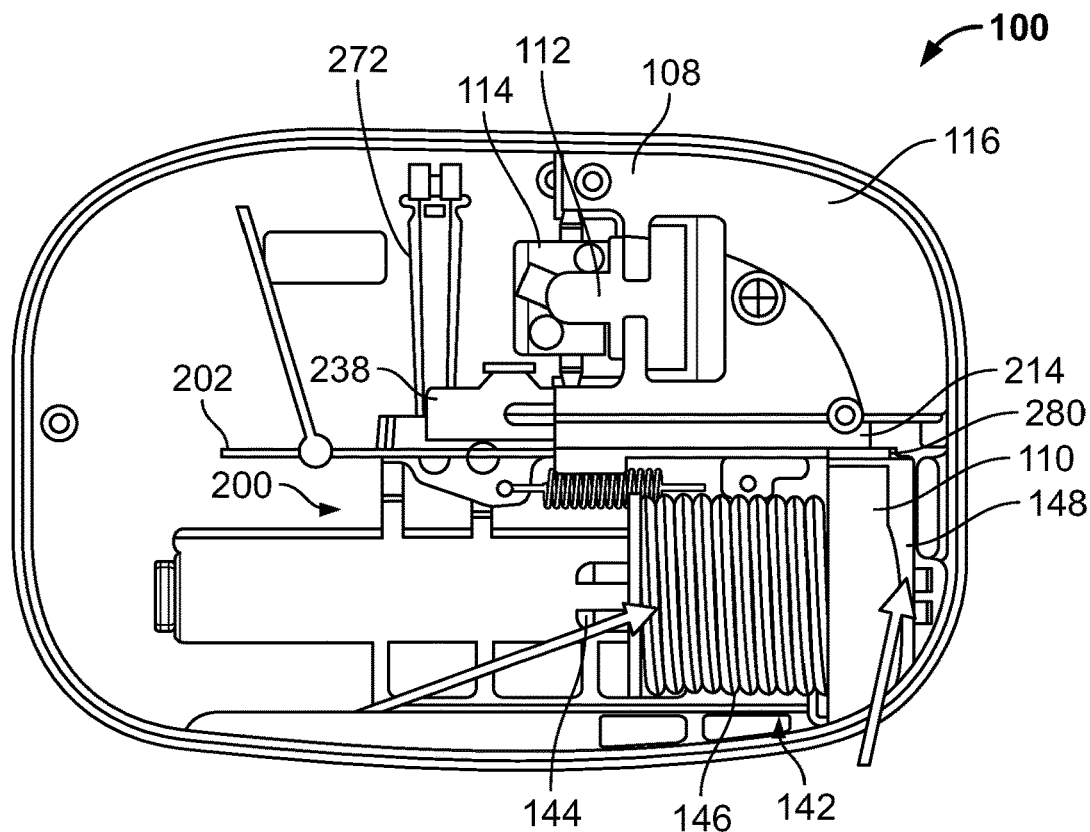
FIG. 12 is a top plan view of a drug delivery device with the escapement assembly of FIG. 10 controlling operation of a plunger drive mechanism in accordance with various embodiments.

Turning now to FIGS. 12 and 13, the escapement assembly 200 is shown in a portion of the drug delivery device 100. In the first through third positions, a switch engagement portion 280 of the foot 214 abuts the stop surface 150 of the release member 148 of the plunger drive mechanism 110. The foot 214 resists lateral movement, optionally with the aid of the bracing members 156, and thereby prevents the torsion spring 146 from releasing. As the slide 202 is shifted to the fourth position, the switch engagement portion 280 of the foot 214 is moved out of engagement with the stop surface 150. Thereafter, the torsion spring 146 releases and drives operation of the plunger drive mechanism 110 to drive the stopper 130 through the reservoir 128 to expel the drug 138 into the flow path 140 and, ultimately, into the patient through the cannula 115.

Advantageously, the slide 202 and pallet 204 can be formed from relatively inexpensive materials, such as sheet metal, and formed into desired shapes. Further, while several muscle wire contractions are described herein, additional pallet stops and corresponding wire contractions can be utilized to activate additional components as desired. For example, an additional step can be added to retract the needle rather than having the retraction performed automatically.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various drug delivery devices and methods for use with a drug delivery device. It should be clear that the drug delivery devices or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number:2 as set forth therein in FIG. 2 and/or the heavy chain of sequence identification number:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers:305-351, including TN8-19-1 through TN8-19-40, TN8-19 con1 and TN8-19 con2; peptibodies of the mL2 family of sequence identification numbers:357-383; the mL 15 family of sequence identification numbers:384-409; the mL 17 family of sequence identification numbers:410-438; the mL20 family of sequence identification numbers:439-446; the mL21 family of sequence identification numbers:447-452; the mL24 family of sequence identification numbers:453-454; and those of sequence identification numbers:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL 1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; b565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but not limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (κ), deposited at the ATCC under number PTA-5220, as described therein; and U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number:1 and sequence identification number:7 respectively therein); 5D (having light chain variable and heavy chain variable sequences sequence identification number:2 and sequence identification number:9 respectively therein); 2H (having light chain variable and heavy chain variable sequences sequence identification number:3 and sequence identification number:10 respectively therein); 43H (having light chain variable and heavy chain variable sequences sequence identification number:6 and sequence identification number:14 respectively therein); 41H (having light chain variable and heavy chain variable sequences sequence identification number:5 and sequence identification number:13 respectively therein); and 15H (having light chain variable and heavy chain variable sequences sequence identification number:4 and sequence identification number:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number:17 and the light chain of sequence identification number:18; those having the heavy chain variable region of sequence identification number:6 and the light chain variable region of sequence identification number:8; those having the heavy chain of sequence identification number:19 and the light chain of sequence identification number:20; those having the heavy chain variable region of sequence identification number:10 and the light chain variable region of sequence identification number:12; those having the heavy chain of sequence identification number:32 and the light chain of sequence identification number:20; those having the heavy chain variable region of sequence identification number:30 and the light chain variable region of sequence identification number:12; those having the heavy chain sequence of sequence identification number:21 and the light chain sequence of sequence identification number:22; those having the heavy chain variable region of sequence identification number:14 and the light chain variable region of sequence identification number:16; those having the heavy chain of sequence identification number:21 and the light chain of sequence identification number:33; and those having the heavy chain variable region of sequence identification number:14 and the light chain variable region of sequence identification number:31, as disclosed in the foregoing publication. A specific antibody contemplated is antibody 1119 as disclosed in the foregoing U.S. publication and having a complete heavy chain of sequence identification number:17 as disclosed therein and having a complete light chain of sequence identification number:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2; Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number:8 and a light chain variable region having sequence identification number:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-a4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL 15 antibody, see U.S. Pat. No. 7,153,507); Tysabri® (natalizumab, anti-a4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (lg domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a531 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL 12 mAb (ABT-874); anti-IL 12/IL23 mAb (CNTO 1275); anti-IL 13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
   an activation assembly including:
      a slide having a main wall portion with an elongate configuration, a plurality of pallet engagement portions spaced from one another along a length of the slide, and a switch engagement portion, the slide being biased to move along a path within the drug delivery device;
      a pallet having a plurality of slide engagement portions, the pallet mounted within the drug delivery device so that at least one of the plurality of slide engagement portions engage at least one of the plurality of pallet engagement portions of the slide; and
      a drive coupled to the pallet, wherein operation of the drive causes the pallet to move relative to the slide to move the plurality of slide engagement portions into and out of engagement with the plurality of pallet engagement portions to thereby allow the slide to move along the path from a first position to a second position;

wherein movement of the slide causes the switch engagement portion to move out of engagement with an activation trigger of a mechanism of the drug delivery device, wherein the switch engagement portion comprises a first switch engagement portion; the slide further comprises a second switch engagement portion; and movement of the slide causes the first switch engagement portion to move out of engagement with an activation trigger of a first mechanism of the drug delivery device and the second switch engagement portion to move out of engagement with an activation trigger of a second mechanism of the drug delivery device.

2. The drug delivery device of claim 1, wherein operation of the drive causes the pallet to move relative to the slide to move the plurality of slide engagement portions into and out of engagement with the plurality of pallet engagement portions to thereby sequentially allow the slide to move along the path from the first position to the second position to a third position to a fourth position; and movement of the slide from the first position to the second position causes the first switch engagement portion to move out of engagement with the activation trigger of the first mechanism and movement of the slide from the third position to the fourth position causes the second switch engagement portion to move out of engagement with the activation trigger of the second mechanism.

3. The drug delivery device of claim 2, further comprising:
- a cannula insertion device including a cannula and a drive assembly coupled to the cannula and configured to shift the cannula downward during an injection operation, the drive assembly having a release engaged by the first switch engagement portion of the slide in the first position and released by the first switch engagement portion in the second position; and
- a plunger rod drive having a release engaged by the second switch engagement portion of the slide in the first, second, and third positions and released by the second switch engagement portion in the fourth position.

4. The drug delivery device of claim 3, wherein the slide further includes a shelf extending outwardly from the main wall portion, the shelf including the first switch engagement portion.

5. The drug delivery device of claim 4, wherein the slide further includes a tab portion extending from the shelf, the tab portion configured to engage the cannula with the slide in the first position and release the cannula with the slide in the second position.

6. The drug delivery device of claim 1, wherein the main wall portion of the slide includes the second switch engagement portion.

7. The drug delivery device of claim 1, wherein a first operation of the drive causes the pallet to move relative to the slide in a first direction to move individual ones of the plurality of slide engagement portions into and out of engagement with individual ones of the plurality of pallet engagement portions to thereby allow the slide to move along the path from a first position to a second position and a second operation of the drive causes the pallet to move relative to the slide in a second, opposite direction to move individual ones of the plurality of slide engagement portions into and out of engagement with individual ones of the plurality of pallet engagement portions allowing the slide to move along the path from the second position to a third position.

8. The drug delivery device of claim 1, wherein the drive comprises a muscle wire having an anchored first end and a second end coupled to the pallet, the pallet is rotatably mounted within the drug delivery device, a first operation comprises a first contraction of the muscle wire in response to reception of an electrical current that causes the pallet to rotate in a first direction to move a first one of the plurality of slide engagement portions out of engagement with a first one of the pallet engagement portions allowing the slide to move along the path from the first position until a second one of the plurality of pallet engagement portions engages a second one of the plurality of slide engagement portions to the second position.

9. The drug delivery device of claim 8, wherein the drive further comprising a biasing mechanism coupled to the pallet to bias the pallet to rotate in a second, opposite direction such that disconnection of the electrical current from the muscle wire causes the pallet to move in the second direction to move the second one of the plurality of slide engagement portions out of engagement with the second one of the pallet engagement portions allowing the slide to move along the path from the second position until a third one of the plurality of pallet engagement portions engages the first one of the plurality of slide engagement portions to a third position.

10. The drug delivery device of claim 9, wherein a second contraction of the muscle wire causes the pallet to rotate in the first direction to move the first one of the plurality of slide engagement portions out of engagement with the third one of the pallet engagement portions allowing the slide to move along the path from the third position to a fourth position.

11. A method for operating a drug delivery device, the method comprising:
- engaging an activation trigger of a mechanism of the drug delivery device with a switch engagement portion of a slide;
- operating a drive to cause a pallet to move relative to the slide to move a plurality of slide engagement portions of the pallet into and out of engagement with a plurality of pallet engagement portions of the slide to thereby shift the slide along a path;
- wherein shifting the slide along the path moves the switch engagement portion of the slide out of engagement with the activation trigger of the mechanism of the drug delivery device to activate the mechanism,
- wherein the switch engagement portion comprises a first switch engagement portion; the mechanism of the drug delivery device comprises a first mechanism of the drug delivery; the slide further comprises a second switch engagement portion; and shifting the slide along the path moves the first switch engagement portion of the slide out of engagement with the activation trigger of the first mechanism of the drug delivery device to activate the first mechanism and subsequently moves the second switch engagement portion of the slide out of engagement with an activation trigger of a second mechanism of the drug delivery device to activate the second mechanism.

12. The method of claim 11, wherein activating activing the first mechanism comprises activating a cannula insertion device including a cannula and a drive assembly configured to shift the cannula downward during an injection operation; and activating the second mechanism comprises activating a plunger rod drive.

13. The method of claim 12, further comprising engaging the cannula with a tab portion of the slide; and wherein moving the first switch engagement portion of the slide out of engagement with the activation trigger of the cannula insertion device further comprises moving the tab portion of the slide out of engagement with the cannula.

14. The method of claim 11, wherein operating the drive to cause the pallet to move relative to the slide to move the plurality of slide engagement portions of the pallet into and out of engagement with the plurality of pallet engagement portions of the slide to thereby shift the slide along the path comprises:
    operating the drive to cause the pallet to move relative to the slide in a first direction to move individual ones of the plurality of slide engagement portions into and out of engagement with individual ones of the plurality of pallet engagement portions to thereby allow the slide to move along the path from a first position to a second position; and
    operating the drive to cause the pallet to move relative to the slide in a second, opposite direction to move individual ones of the plurality of slide engagement portions into and out of engagement with individual ones of the plurality of pallet engagement portions allowing the slide to move along the path from the second position to a third position.

15. The method of claim 11, wherein the drive comprises a muscle wire having an anchored first end and a second end coupled to the pallet, the pallet is rotatably mounted within the drug delivery device, and operating the drive to cause the pallet to move relative to the slide to move the plurality of slide engagement portions of the pallet into and out of engagement with the plurality of pallet engagement portions of the slide to thereby shift the slide along the path comprises directing an electrical current to the muscle wire to cause the pallet to rotate in a first direction to move a first one of the plurality of slide engagement portions out of engagement with a first one of the pallet engagement portions allowing the slide to move along the path from the first position until a second one of the plurality of pallet engagement portions engages a second one of the plurality of slide engagement portions to the second position.

16. The method of claim 15, further comprising:
    disconnecting the electrical current from the muscle wire, such that a biasing member causes the pallet to move in an opposite, second direction to move the second one of the plurality of slide engagement portions of the pallet out of engagement with the second one of the pallet engagement portions of the slide; and
    shifting the slide along the path from the second position until a third one of the plurality of pallet engagement portions engages the first one of the plurality of slide engagement portions to a third position.

17. The method of claim 16, further comprising:
    directing an electrical current to the muscle wire to cause a second contraction of the muscle wire to cause the pallet to rotate in the first direction to move the first one of a plurality of slide engagement portions of the pallet out of engagement with the third one of the plurality of pallet engagement portions of the slide; and
    shifting the slide along the path from the third position to a fourth position.

18. A drug delivery device comprising:
    an activation assembly including:
        a slide having a main wall portion with an elongate configuration, a plurality of pallet stops spaced from one another along a length of the slide, and a switch stop, the slide being biased to move along a path within the drug delivery device;
        a pallet having a plurality of outwardly projecting tabs, the pallet rotatably mounted within the drug delivery device so that the plurality of tabs selectively engage at least one of the plurality of pallet stops; and
        muscle wire having an anchored first end and a second end coupled to the pallet,
    wherein a first contraction of the muscle wire in response to reception of an electrical current causes the pallet to rotate in a first direction to move a first one of the plurality of tabs out of engagement with a first one of the pallet stops allowing the slide to move along the path from a first position until a second one of the plurality of pallet stops engages a second one of the plurality of tabs to a second position;
    wherein movement of the slide causes the switch stop to move out of engagement with an activation trigger of a mechanism of the drug delivery device,
    wherein the switch stop comprises a first switch engagement portion; the slide further comprises a second switch engagement portion; and movement of the slide causes the first switch engagement portion to move out of engagement with an activation trigger of a first mechanism of the drug delivery device and the second switch engagement portion to move out of engagement with an activation trigger of a second mechanism of the drug delivery device.

* * * * *

UNITED STATES PATENT AND TRADEMARK OFFICE
CERTIFICATE OF CORRECTION

PATENT NO. : 12,042,642 B2
APPLICATION NO. : 17/264157
DATED : July 23, 2024
INVENTOR(S) : Sudeshna Dutta Ray et al.

Page 1 of 1

It is certified that error appears in the above-identified patent and that said Letters Patent is hereby corrected as shown below:

In the Claims

At Column 23, Line 6, "position;" should be -- position, --.

At Column 24, Line 66, "activating activing" should be -- activating --.

At Column 26, Line 37, "position;" should be -- position, --.

Signed and Sealed this
Twenty-fifth Day of February, 2025

Coke Morgan Stewart
*Acting Director of the United States Patent and Trademark Office*